United States Patent
Jüsten et al.

(10) Patent No.: US 9,289,460 B2
(45) Date of Patent: Mar. 22, 2016

(54) USE OF NATURAL ACTIVE SUBSTANCES IN COSMETIC OR THERAPEUTIC COMPOSITIONS

(71) Applicants: Peter Jüsten, Rueil-Malmaison (FR); Dominique Marie Noelle Borreill, Chennevieres sur Marne (FR); William Marques, Rueil-Malmaison (FR)

(72) Inventors: Peter Jüsten, Rueil-Malmaison (FR); Dominique Marie Noelle Borreill, Chennevieres sur Marne (FR); William Marques, Rueil-Malmaison (FR)

(73) Assignee: Lesaffre et Compagnie, Paris (FR)

( * ) Notice: Subject to any disclaimer, the term of this patent is extended or adjusted under 35 U.S.C. 154(b) by 32 days.

(21) Appl. No.: 13/926,707

(22) Filed: Jun. 25, 2013

(65) Prior Publication Data

US 2013/0287715 A1    Oct. 31, 2013

Related U.S. Application Data (62) Division of application No. 12/867,193, filed as application No. PCT/IB2009/000237 on Feb. 11, 2009, now abandoned.

(30) Foreign Application Priority Data

Feb. 12, 2008    (FR) ..................................... 08 00754

(51) Int. Cl.
| A61K 36/06 | (2006.01) |
| A61K 38/01 | (2006.01) |
| A61K 8/02 | (2006.01) |
| A61K 8/99 | (2006.01) |
| A61Q 5/00 | (2006.01) |
| A61Q 5/12 | (2006.01) |
| A61Q 7/00 | (2006.01) |
| A61Q 19/00 | (2006.01) |
| A61Q 19/08 | (2006.01) |
| A61K 8/64 | (2006.01) |

(52) U.S. Cl.
CPC ............... *A61K 38/01* (2013.01); *A61K 8/0212* (2013.01); *A61K 8/64* (2013.01); *A61K 8/99* (2013.01); *A61Q 5/00* (2013.01); *A61Q 5/006* (2013.01); *A61Q 5/12* (2013.01); *A61Q 7/00* (2013.01); *A61Q 19/00* (2013.01); *A61Q 19/007* (2013.01); *A61Q 19/008* (2013.01); *A61Q 19/08* (2013.01)

(58) Field of Classification Search
None
See application file for complete search history.

(56) References Cited

U.S. PATENT DOCUMENTS

| 3,852,502 A | * | 12/1974 | Bishov et al. | ................. 426/544 |
| 4,929,555 A | * | 5/1990 | Cregg et al. | ................. 435/6.16 |
| 5,397,770 A | * | 3/1995 | Levin et al. | .................... 514/7.6 |

(Continued)

FOREIGN PATENT DOCUMENTS

| BE | 841216 A | * | 10/1976 |
| EP | 0695801 A2 | * | 2/1996 |

(Continued)

OTHER PUBLICATIONS

Springer 'Yeast Peptone HYP-A' Online, URL<http://www.biospringer.com/cc_index.php?tag=Yeast+peptone+for+fermentation+and+culture+media&cc-parametresurl=Y2MtcnVicmlxdWVwYWdlcz1CSU9-URUMmY2MtcGFnZT1QQUdFX0dBTU1FX0JTJmNj-LWdhbW1IX2JzPUJJT1RFQ19TUFJJTkdFUkhZUCZjYy1s-YW5ndWU9RU4=&PHPSESSID=db4133ac6356ba25-5d82b9d520fe6581 > accessed 6.*

(Continued)

*Primary Examiner* — Patricia A Leith
(74) *Attorney, Agent, or Firm* — IP Attorneys Group, LLC (57) ABSTRACT

The invention relates to cosmetic or therapeutic compositions that contain hydrolyzed yeast proteins as an active ingredient, to the use of said cosmetic or therapeutic compositions, and to a method for cosmetic treatment.

18 Claims, 1 Drawing Sheet

(56) References Cited

U.S. PATENT DOCUMENTS

| | | | | |
|---|---|---|---|---|
| 5,753,214 | A | * | 5/1998 | Yoshioka et al. ............ 424/70.2 |
| 6,228,968 | B1 | * | 5/2001 | Yoshioka et al. ............... 528/38 |
| 2002/0187167 | A1 | * | 12/2002 | Vacher et al. ................. 424/401 |
| 2008/0085287 | A1 | * | 4/2008 | Auclair et al. ........... 424/195.16 |
| 2008/0188415 | A1 | * | 8/2008 | Koruga ........................... 514/12 |

FOREIGN PATENT DOCUMENTS

| | | | | |
|---|---|---|---|---|
| GB | 1032687 | A | * | 6/1966 |
| JP | 08048698 | A | * | 2/1996 |
| KR | 2003071893 | A | * | 9/2003 |

OTHER PUBLICATIONS

Wikipedia: Papain; Online, URLhttp://en.wikipedia.org/wiki/Papain, 5 pages, accessed Aug. 7, 2012.*

Wikipedia; Phosphonate, Online, URLhttp://en.wikipedia.org/wiki/Phosphonate accessed Aug. 7, 2012, 4 pages.*

Project EU 22704 Competence Center of Food and Fermentation Technologies; Activity Report, Tallinn, 2007, 53 pages.*

Kollar et al. Architecture of the Yeast Cell Wall 6(1→6)-Glucan Interconnects Mannoprotein, β(1→3)-Glucan, and Chitin; Journal of Biological Chemistry, 272, pp. 17762-17775.*

Klis et al. Cell Wall Construction in *Saccharomyces cerevisiae*; Yeast, 2006 (23), 185-202.*

NewsRx: Drug Week, May 2, 2008; 2171.*

Barankin, B. Patient Care 15.7, Jul. 2004: 30.*

Wikipedia, Online,: Yeast; URL<http://en.wikipedia.org/wiki/Yeast> 6 pages.*

Raskin et al. Can an Apple a Day Keep the Doctor Away? Current Pharmaceutical Design, 2004, 10, 3419-3429.*

H.B. MacPhillamy: Drugs From Plants; Plant Science Bulletin, Botanical Society of America, vol. 9, No. 2, Apr. 1963.*

* cited by examiner

USE OF NATURAL ACTIVE SUBSTANCES IN COSMETIC OR THERAPEUTIC COMPOSITIONS

CROSS REFERENCE TO RELATED APPLICATIONS

This application is a divisional of U.S. patent application Ser. No. 12/867,193, filed on Aug. 11, 2010, which is a national phase filing of International Patent Application PCT/IB2009/000237 filed on Feb. 11, 2009 which designates the United States, and which claims the priority of French Patent Application No. FR0800754 filed on Feb. 12, 2008. The contents of all of the above mentioned Applications are relied upon and incorporated herein by reference in their entirety.

FIELD OF THE INVENTION

The purpose of this invention is the use of natural active substances in cosmetic and in therapeutic compositions, these substances being hydrolysed yeast proteins obtained from the insoluble yeast fraction.

TECHNICAL BACKGROUND

For several years, protein hydrolysates have given rise to an interest in cosmetic and therapeutic applications.

Protein hydrolysates can have different origins: animal, in particular fish, vegetable, or fungal, for example yeast.

The presence or absence of biological activity of a protein hydrolysate depends, in particular, on the nature of the start proteins.

Thus, the hydrolysis of fish proteins allowed obtaining hydrolysed proteins with a particular spatial structure recognised by certain receptors. Activities of hormonal and opioid type have thus been emphasised (Legal and Stenherg. Biofutur, No. 179, 1998, pages 61 to 63).

Certain documents of the prior art mention the use of yeast protein hydrolysates in cosmetic compositions. These yeast protein hydrolysates are obtained either through the hydrolysis of yeast whole cells or through the hydrolysis of the yeast soluble fraction (the cytoplasmic content).

Thus, application patent EP 0 695 801, describes the cosmetic use of a peptide composition obtained through:
  a stage of yeast thermal treatment followed by a treatment with lytic enzymes of the yeast cell wall, in order to obtain a blending,
  a protein purification and separation stage of the aforesaid blending, in order to obtain yeast proteins, and
  an hydrolyse state of the aforesaid proteins.

The lytic enzymes of the cell wall used in this document are enzymes attacking glucans and destabilising the wall and membrane. Thus, such a composition has hydrolysed proteins obtained from the yeast soluble fraction.

Patent application EP 0 126 364, describes the cosmetic use of a product with no histamine, non-pyrogenic, sterile, active obtained through a process comprising the following stages:
  yeast plasmolysis and homogenisation to a temperature lower than 0° C.,
  treatment with a proteolytic enzyme for at least 70 hours,
  treatment with a diamine oxidase in order to eliminate substances having histamine,
  fractional precipitation with a blending of alcohols in order to eliminate residual proteins.

Thus, the final product has yeast-hydrolysed proteins obtained from the hydrolysis of whole yeast proteins. The implementation of such a production process shows many drawbacks, in particular, the duration of the process, the multiplicity of stages and the need of working under sterile conditions.

Application patent of EP 0 237 398, describes the cosmetic use of polypeptides biologically active obtained through the process comprising the following stages:
  mechanical crushing of natural substances, for example yeasts, in order to obtain an aqueous homogenate,
  enzymatic hydrolysis with a hydrolysis agent consisting of α-chymotrypsin and possibly trypsin, in order to obtain an hydrolysate,
  separation of a polypeptide fraction with a specific molecular weight.

Thus, the polypeptide fraction derives from the protein hydrolysis obtained from whole yeasts. In particular, the polypeptide fraction has a molecular weight lower than 10,000 Da and higher than 1,000 Da.

Consumers increasingly require <<natural>> products, whether in the food, cosmetic or pharmaceutical field.

In the cosmetic and pharmaceutical field, there is a real need to give new active natural substances that:
  have improved cosmetic or therapeutic qualities, such as moisturising, anti-aging effects and/or firmness; and/or
  an excellent stability in time; and/or
  the production of which is homogeneous and/or the production process is easily implemented on industrial scale.

SUMMARY OF THE INVENTION

The purpose of this invention is the supply of natural active substances useful in the cosmetic or therapeutic field.

A purpose of the invention is also the supply of new cosmetic or therapeutic compositions.

Another purpose of the invention relates to a method for cosmetic treatment for skin and/or skin appendages and/or mucous membranes or these substances for their therapeutic use.

This invention is based, in particular, on the discovery of a new category of hydrolysed proteins with improved cosmetic and/or therapeutic activities, and/or an excellent stability in time, and/or the production of which is homogeneous and/or the production process is easily implemented on industrial scale.

The purpose of this invention is a cosmetic or therapeutic composition comprising yeast hydrolysed proteins as active substance, characterised in that the said yeast hydrolysed proteins are obtained from yeast insoluble fraction.

According to an embodiment, the yeast-hydrolysed proteins are obtained through enzymatic hydrolysis and/or acid hydrolysis and/or alkaline hydrolysis.

According to an embodiment, the yeast hydrolysed proteins are obtained through enzymatic hydrolysis with at least one peptidase, preferably chosen among papain, trypsin, chymotrypsin, subtilisin, pepsin, thermolysin, pronase, flavastacine, enterokinase, factor Xa protease, Turin, bromelain, proteinase K, genenase I, thermitase, carboxypeptidase A, carboxypeptidase B, collagenase and/or their blending.

According to an embodiment, the yeast hydrolysed proteins are obtained from yeasts of *Saccharomyces, Kluyveromyces, Torula, Candida, Hansenula, Pichia* genus, and/or their blending, preferably *Saccharomyces*, advantageously *Saccharomyces cerevisiae*.

According to an embodiment, the yeast-hydrolysed proteins have at least 40%, preferably at least 45%, more preferably at least 50%, even more preferably at least 55%, even more preferably at least 60% of yeast proteins with a molecular weight ranging between 1 and 5 kDa.

According to an embodiment, the yeast-hydrolysed proteins have at most 55%, preferably at most 50%, more preferably at most 45%, even more preferably at most 40%, even more preferably at most 35% of hydrolysed yeast proteins with a molecular weight lower than 1 kDa.

According to an embodiment, the AN/TN ratio of the hydrolysed yeast proteins is lower or equal to 35%, in particular lower or equal to 30%, in particular lower or equal to 25%, in particular lower or equal to 20%.

According to an embodiment, the composition has from 0.001% to 20% of hydrolysed yeast proteins, more preferably from 0.001% to 15% of hydrolysed yeast proteins, even more preferably from 0.001% to 10% of hydrolysed yeast proteins, even more preferably from 0.01% to 3% of hydrolysed yeast proteins, even still more preferably from 0.01% to 2% of hydrolysed yeast proteins.

According to an embodiment, the composition comprises at least one additive chosen among preservatives, chelating agents, colouring agents, UV filter, pH regulator, texturising agents, perfume or antioxidant, and/or at least one excipient chosen among hydrophilic compounds, hydrophobic compounds or surface active agents.

The purpose of this invention is also a preparation process of a cosmetic or therapeutic composition, consisting of the following stages:
protein hydrolysis of the yeast insoluble fraction in order to obtain hydrolysed yeast proteins, and
blending of the said hydrolysed yeast proteins with an acceptable cosmetic or therapeutic vehicle.

The purpose of this invention is the use of hydrolysed yeast proteins obtained from the yeast insoluble fraction as active substance in cosmetic and/or therapeutic compositions.

Another purpose of this invention relates to a method for cosmetic treatment comprising a stage of contact with the skin and/or skin appendages and/or mucous membranes of a composition according to this invention or liable to be obtained through the process according to this invention.

Another purpose of this invention relates also to the hydrolysed yeast proteins obtained from the yeast insoluble fraction for their use as medicine, preferably for the treatment and/or prevention of pathological dry skin, pathological healing problems and/or pathological hyperseborrhoea, and/or acne.

DETAILED DESCRIPTION OF THE EMBODIMENTS

The purpose of this invention is a cosmetic or therapeutic composition comprising hydrolysed yeast proteins as active substance.

In particular, the purpose of this invention is a cosmetic or therapeutic composition comprising hydrolysed yeast proteins as active substance characterised in that the said yeast hydrolysed proteins are obtained from yeast insoluble fraction.

The hydrolysed yeast proteins are also called <<yeast peptones>> or <<yeast peptides obtained through hydrolysis>>.

By <<cosmetic composition>>, it is here designated a composition intended to cause a cosmetic effect.

According to a preferred embodiment of this invention, the cosmetic effect is obtained through a local application of the compositions according to this invention.

The term <<local>> indicates that the composition is active in the place where it is applied, on the skin, skin appendages, and/or mucous membranes. According to the invention, the composition may simultaneously target the superficial layers of the epidermis and/or the dermis.

By the term <<skin appendage>>, it is designated generally everything that covers the skin, and in particular hair, nails, hairs, eyelashes.

The term <<skin>> includes the scalp.

The term <<skin>> includes the dermis and the epidermis, as well as the superficial layers of the epidermis.

By the term <<mucous membranes>> or the term <<humid epithelial tissue>> it is designated the membranes that cover the open cavities towards the external medium, and in particular the oral, nasal and genital mucosae, as well as the vaginal mucosae.

In another preferred embodiment, the cosmetic effect is obtained through administration by mouth.

By <<therapeutic composition>> it is designated a composition intended to cause a therapeutic effect.

A preferred therapeutic composition, according to the invention, is a dermatological composition.

In particular, the therapeutic effect is obtained through a local application of therapeutic compositions according to this invention.

Hence, the purpose of this invention is also a cosmetic or therapeutic composition as defined above, intended for an application on the skin and/or skin appendages and/or mucous membranes.

Another preferred composition according to the invention, is a composition suitable for administration by mouth.

By <<active substance>> or <<active principle>> or <<active matter>>, it is designated here the substance responsible for the cosmetic effect within a cosmetic composition or responsible for the therapeutic effect within a therapeutic composition.

A cosmetic composition, according to the invention, comprises at least a compound as active substance and an acceptable cosmetic vehicle.

A therapeutic composition, according to the invention, comprises at least a compound as active substance and an acceptable therapeutic vehicle.

The hydrolysed yeast proteins, according to the invention, are obtained from the yeast insoluble fraction.

By <<insoluble fraction>> it is designated the yeast hulls, that is to say, the wall and plasmic membrane of the yeasts at a time.

The insoluble fraction represents about 20 to 30% by mass dry matters of the yeast cells.

By <<soluble fraction>> it is designated the content of the yeast, other than the yeast hulls.

Yeast hulls have essentially carbohydrates (about 50%). Proteinic matters represent about 10 to 20% of yeast hulls, in particular, about 13 to 18% of yeast hulls (by mass of fry matters).

The insoluble fraction can be obtained through a thermal treatment of the yeast during 1 to 3 hours between 70° C. and 90° C., followed by a separation of the soluble and insoluble fraction, especially through centrifugation. Hence, the soluble fraction is eliminated and the insoluble fraction is recovered.

The hydrolysed yeast proteins, according to this invention, are obtained through hydrolysis of the proteins obtained from the yeast insoluble fraction.

The hydrolysed yeast proteins can be submitted to specific complementary treatments (for example, separation of the proteins through centrifugation, concentration, filtration, or activated charcoal treatment).

Thus, unlike the traditional protein hydrolysates, obtained after an autolysis or an enzymatic hydrolysis of the whole cell content or of the soluble part only, the hydrolysed yeast proteins, according to this invention, are obtained from a particular cellular fraction. The proteins of the yeast insoluble fraction have in fact a different nature than those present in the yeast soluble fraction. The proteins of the yeast insoluble fraction have, in particular, mannoproteins that have no cellular fraction.

In addition, the proteins of the insoluble fraction are essentially native proteins, not subjected to hydrolysis, whereas most of the proteins of the soluble fraction have already been subjected to partial or total hydrolysis. Thus, the result of the hydrolysis carried out starting from the proteins obtained from whole yeast is less verifiable due to the heterogeneity of the status of the start proteins.

In addition, the process, according to this invention, allows making the proteins of the insoluble fraction more accessible to hydrolysis, among other things through a strong concentration of the said proteins, with respect to a hydrolysis carried out on whole yeast.

Thus, the hydrolysed yeast proteins, according to this invention, are characterised in that a particular peptide nature, a particular (and homogeneous) profile of peptide molecular distribution, and/or a specific AN/TN ratio (with very low free amino acids), namely, in particular, an AN/TN ratio of hydrolysed yeast proteins lower or equal to 35%, in particular, lower or equal to 30%, in particular, lower or equal to 25%, in particular, lower or equal to 20%.

By <<AN/TN ratio>> it is designated the ratio of the amino acids nitrogen quantity (in percentage) on the by mass nitrogen quantity (in percentage). The AN/TN ratio indicates the protein degradation rate, in particular the hydrolysis degree of the yeast proteins.

Surprisingly, this new source of yeast proteins, once hydrolysed, has cosmetic and therapeutic activities.

The hydrolysed yeast proteins present in a dry form, especially as powder, or under solution, for example under aqueous solution.

The purpose of this invention is a cosmetic or therapeutic composition as defined above, characterised in that the yeast hydrolysed proteins are obtained through enzymatic hydrolysis and/or acid hydrolysis and/or alkaline hydrolysis.

The acid hydrolysis is a hydrolysis obtained in an acidic medium, preferably in the heat, for example by using a strong acid such as hydrochloric acid, sulphuric acid, phosphoric acid, and/or nitric acid.

In particular, the acid hydrolysis destroys the tryptophan and turns the glutamine and aspargine amino acids into glutamate and aspartate, respectively.

The alkaline hydrolysis is a hydrolysis obtained in an alkaline medium, for example by using a strong base such as sodium hydroxide and potassium hydroxide.

In particular, the alkaline hydrolysis destroys serine, threonine, and cysteine amino acids.

The enzymatic hydrolysis of the yeast proteins is carried out through hydrolases.

According to a preferred embodiment, the yeast-hydrolysed proteins, according to this invention, are obtained through enzymatic hydrolysis.

The enzymatic hydrolysis is carried out by adding at least one exogenous enzyme. Preferably, the yeast exogenous enzymes have been deactivated beforehand, for example through a thermal treatment.

In particular, according to this invention, the hydrolases are hydrolases acting on peptide bonds. Such hydrolases called peptidases or proteases or proteolytic enzymes have number EC 3.4 in the EC classification. Peptidases catalyse the hydrolytic cleavage of the C—N bond.

In particular, according to this invention, the hydrolases are chosen among esopeptidases, especially aminopeptidase, dipeptidase, dipeptidyl-peptidase, tripeptidyl-peptidase, peptidyl-dipeptitase, carboxypeptidase of serine type, carboxypeptidase of cysteine type, metallocarboxypeptidase, omega-peptidase, and endopeptidases (or proteinase), in particular serine endopeptidase, cysteine endopeptidase, aspartic endopeptidase, and metalloendopeptidase.

The enzymatic hydrolysis can be coupled to a disulfide bridge hydrolysis, carried out through reducing agents, for example the 2-mercaptoethanol or the dithiothreitol, the TCEP (Tris (2-carboxyethyl) phosphine).

Particularly, the purpose of this invention is a cosmetic or therapeutic composition as defined above, characterised in that the yeast hydrolysed proteins are obtained through enzymatic hydrolysis with at least one peptidase, preferably chosen among papain, trypsin, chymotrypsin, subtilisin, pepsin, thermolysin, pronase, flavastacine, enterokinase, factor Xa protease, furin, bromelain, proteinase K, genenase I, thermitase, carboxypeptidase A, carboxypeptidase B, collagenase, Alcalase®, Neutrase® and/or their blending.

The conditions of use of the enzymes (in particular, their concentration, duration of hydrolysis, temperature) are easily determined by a skilled person in the art.

As an example, the hydrolysis can be carried out by adding proteases for at least 18 hours between 45° C. and 55° C.

Preferably, the solubilised part having yeast hydrolysed proteins is then recovered through centrifugation, before being possibly concentrated, and then dried.

A preferred enzyme, according to this invention, is chosen among papain, trypsin, pepsin, Alcalase®, Neutrase®.

According to a particular embodiment, the enzymatic hydrolysis is obtained with at least two different enzymes, in particular with at least three different enzymes, in particular with at least four different enzymes.

As an example, the hydrolysis can be carried out with a blending of papain and Alcalase®.

In particular, this invention relates to a cosmetic or therapeutic composition as defined above, characterised in that the yeast hydrolysed proteins are obtained from yeasts of *Saccharomyces, Kluyveromyces, Torula, Candida, Hansenula, Pichia* genus, and/or their blending, preferably *Saccharomyces,* advantageously *Saccharomyces cerevisiae.*

The yeast hydrolysed proteins obtained from yeasts of *Hansenula* genus, are preferably *Hansenula anomala* yeasts.

The yeast hydrolysed proteins obtained from yeasts of *Pichia* genus, are preferably *Pichia pastoris* yeasts.

The yeast hydrolysed proteins, according to this invention, are preferably obtained from *Saccharomyces,* advantageously *Saccharomyces cerevisiae.*

According to this invention, a preferred cosmetic and therapeutic composition have, as active substance, hydrolysed yeast proteins obtained from yeasts of the same genus, and preferably of the same kind and same species of yeast.

According to another embodiment, the cosmetic and therapeutic composition have, according to this invention, as active substance, hydrolysed yeast proteins obtained from yeasts of the same genus, but with at least two different species, in particular at least three different species.

According to another embodiment, the cosmetic and therapeutic composition have, according to this invention, as active substance, hydrolysed yeast proteins obtained from yeasts of at least two different genera, in particular at least three different genera.

This invention relates particularly to a cosmetic or therapeutic composition as defined above, characterised in that the yeast hydrolysed proteins have at least 40%, preferably at least 45%, more preferably at least 50%, even more preferably at least 55%, even more preferably still at least 60% of yeast proteins with a molecular weight ranging between 1 and 5 kDa.

This invention relates particularly to a cosmetic or therapeutic composition as defined above, characterised in that the yeast hydrolysed proteins have at most 55%, preferably at most 50%, more preferably at most 45%, even more preferably at most 40%, even more preferably still, at most 35% of hydrolysed yeast proteins with a molecular weight lower than 1 kDa.

This invention relates particularly to a cosmetic or therapeutic composition as defined above, characterised in that the AN/TN ratio of the hydrolysed yeast proteins is lower or equal to 35%, in particular lower or equal to 30%, in particular lower or equal to 25%, in particular lower or equal to 20%.

By <<AN/TN ratio>> it is designated the ratio of the amino acids nitrogen quantity (in percentage) on the by mass nitrogen quantity (in percentage). The AN/TN ratio indicates the protein degradation rate, in particular the hydrolysis degree of the yeast proteins.

According to this invention, a preferred composition have yeast hydrolysed proteins of which at least 55% of said proteins have a molecular weight ranging between 1 and 5 kDa, and/or at most 42% of said proteins have a molecular weight lower than 1 kDa, and/or the AN/TN ratio is lower or equal to 35%.

According to this invention, another preferred composition has yeast hydrolysed proteins of which at least 60% of said proteins have a molecular weight ranging between 1 and 5 kDa, and/or at most 37% of said proteins have a molecular weight lower than 1 kDa, and/or the AN/TN ratio is lower or equal to 35%.

According to a preferred embodiment, this invention relates to a cosmetic or therapeutic composition as defined above, in which the hydrolysed yeast proteins are obtained from the product Springer® Hydrolyzed Yeast Peptone-A.

The product Springer® Hydrolyzed Yeast Peptone-A have hydrolysed yeast proteins obtained from the insoluble fraction of *Saccharomyces cerevisiae*. The hydrolysed yeast proteins of the product Springer® Hydrolyzed Yeast Peptone-A have most of the hydrolysed proteins with a molecular weight higher or equal to 1 kDa and lower than 5 kDa (about 60%); the other hydrolysed proteins have essentially a molecular weight lower than 1 kDa (about 32%) (see example 1).

The hydrolysed yeast proteins of the product Springer® Hydrolyzed Yeast Peptone-A are characterised in that an AN/TN ratio ranging between 15 and 28%.

According to this invention, the composition can have the product Springer® Hydrolyzed Yeast Peptone-A, or hydrolysed yeast proteins obtained through supplementary extraction and/or purification stages starting from the said product.

According to the invention, the composition can have hydrolysed yeast proteins corresponding to a specific hydrolysed protein fraction isolated from the Springer® Hydrolyzed Yeast Peptone-A product.

According to the invention, a preferred cosmetic or therapeutic composition has the product Springer® hydrolyzed Yeast Peptone-A.

This invention relates particularly to a cosmetic or therapeutic composition as defined above, having from 0.001% to 20% of hydrolysed yeast proteins, more preferably from 0.001% to 15% of hydrolysed yeast proteins, even more preferably from 0.001% to 10% of hydrolysed yeast proteins, even more preferably from 0.01% to 3% of hydrolysed yeast proteins, even more preferably from 0.01% to 2% of hydrolysed yeast proteins.

The percentages are given in weight/weight.

This invention relates in particular to a cosmetic or therapeutic composition as defined above, having from 0.01% to 20% of hydrolysed yeast proteins, in particular from 0.01% to 15% of hydrolysed yeast proteins, in particular from 0.01% to 10% of hydrolysed yeast proteins.

Object of this invention is more particularly a cosmetic or therapeutic composition as defined above, having from 0.01% to 3% of hydrolysed yeast proteins, in particular from 0.01% to 2% of hydrolysed yeast proteins, in particular from 0.01% to 1% of hydrolysed yeast proteins.

According to the invention, an acceptable cosmetic or therapeutic vehicle have preferably at least a compound as additive and at least a compound as excipient, since such a compound can be used in many ways.

This invention relates to a cosmetic or therapeutic composition as defined above, characterised in that the fact that it have at least one additive chosen among preservatives, chelating agents, colouring agents, UV filter, pH regulator, texturising agents, perfume or antioxidant, and at least one excipient chosen among hydrophilic compounds, hydrophobic compounds or surface active agents.

By <<additive>>, it is designated an agent that plays in the cosmetic or therapeutic composition a role of preservative, chelating agent, colouring agent, UV filter (allowing to protect raw materials), pH regulator (acid or base), texturising agent, perfume and/or antioxidant.

By <<raw materials to be protected>>, it is designated every compound of the cosmetic or therapeutic composition liable to be degraded by light.

By <<excipient>>, it is designated the hydrophilic compounds that constitute an aqueous phase, the hydrophobic or lipophile compounds that constitute a fatty phase or surface active agents.

Surface active agents are amphiphilic molecules able to keep together two mediums, normally non mixable, by lowering their interfacial tensions.

Surface active agents are ionic (anionic, cationic or amphoteric) or non-ionic.

According to this invention, the following list of compounds that can be used in the cosmetic or therapeutic vehicle, is given by way of example and must not be considered exhaustive.

According to this invention, the preservatives used in the compositions are especially chosen among butylated hydroxytoluene (BHT), butylated hydroxyanisole (BHA), propyl gallate, octyl, dodecyl, α-tocopherol, α-tocopherol acetate, ascorbic acid, ascorbyl palmitate, rosemary extracts, gingko biloba extracts, and orizanol.

According to this invention, the chelating agents used in the compositions are especially chosen among citric acid, cyclodextrin, EDTA disodium, pentasodium pentetate, phytic acid, sodium citrate, sodium phytate, and EDTA or tetrasodium pyrophosphate.

According to this invention, the colouring agents used in the compositions are especially chosen among colouring agents with CI denomination (Color Index).

According to this invention, the UV filters used in the compositions are especially chosen among benzophenone-3 (oxybenzone), benzophenone-4 (sulisobenzone), drometrizole, trisiloxane, benzyl salicytate, avobenzone, octyl methoxycinnamate (octinoxate), ethylhexyl salicytate (octisalate) or titanium dioxide.

According to this invention, the pH regulators (acid or base) used in the compositions are especially chosen among aminomethyl propanol, citric acid, fumaric acid, orthophosphoric acid, sebacic acid (decanedioic acid), sodium acetate, sodium bicarbonate, sodium citrate, sodium hydroxide, tartaric acid, tetrasodium pyrophosphate or triethylamine (TEA).

By <<texturising agent>>, it is designated an agent able to increase the viscosity of aqueous phases in which it is dispersed, the increase being advantageously high.

According to the circumstances, a texturising agent can be a thickening agent and/or a gelling agent.

By <<thickening agent>>, it is designated a substance that allows to obtain a viscous solution without forming a 3D network, in particular, as opposed to gelling agents.

Texturising agents are especially chosen among agar-agar or gelose, alginates, carraghenates, guar gum, tara gum, carob gum, gum adragant, karaya gum, xanthan gum, aloe gel, starch glycerol, chitosan, silica, silicates, —in particular bentonite, hectorite, montmorillonite, aluminium silicate, magnesium silicate—, cellulose derivatives, in particular hydroxyethyl cellulose, hydroxypropyl cellulose, methylhydroxypropylcellulose or hypromellose, acrylic and vinyl polymers, —in particular carbomers, cyanoacrylate polymers, polyvinylpyrrolidone (PVP), polyvinyl alcohols—, polyethylene glycols, and polyquaterniums.

According to the invention, the perfumes used in the compositions are especially chosen among essential oils, compositions with synthetic origin, solubilised perfumes.

According to the invention, the antioxidants used in the compositions are especially chosen among ascorbyl palmitate, BHT, Tocopherol (E Vitamin), and tocopheryl acetate.

Hydrophilic compounds of the aqueous phase are especially chosen among water, alcohols, and polyols.

According to the invention, the alcohols that can be used in the compositions are especially ethanol, propanol, isopropanol, benzyl alcohol, and hexyl alcohol.

According to the invention, the polyols that can be used in the compositions are especially glycerol, propylene glycol, butylene glycol, hexylene glycol, and sorbitol.

Hydrophobic compounds of the fatty phase are especially chosen among hydrocarbons, fatty acids, fatty alcohols, esters, glycerides, cerides, and phosphatides.

Hydrocarbons are especially chosen among carbon and hydrogen chains, saturated and unsaturated, linear, ramified or cyclical, in particular carbon chains from 22 to 35 carbon and in particular among the following hydrocarbons: paraffins, paraffin oils, vaseline, squalane, silicones, and perhydrosqualenes.

According to the invention, the silicones that can be used in the compositions are especially volatile silicone oils, non-volatile silicone oils, modified silicone oils, silicone waxes, silicone gums, silicone emulsions, silicone microemulsions. Silicones are especially chosen among polyloxane silicones, polydimethylsiloxanes or dimethicones, phenyl trimethyl siloxanes or phenyl methicones, cyclical polydimethylsiloxanes or cyclomethicones, dimethicone copolyols, amodimethicones, and dimethicone propyl PG-Betaine.

According to the invention, the fatty acids used in the compositions are especially saturated fatty acids or unsaturated fatty acids, in particular monounsaturated, diunsaturated, triunsaturated fatty acids. Fatty acids are especially chosen among stearic acid, palmitic acid, lauric acid, myristic acid, oleic acid, linoleic acid, and linolenic acid.

Fatty alcohols are especially chosen among long chain saturated fatty alcohols, —cetylic alcohol or hexadecanol, stearyl alcohol, cetostearyl alcohol—short chain unsaturated fatty alcohols, —oleic alcohol, octyldodecanol, and tetrahydrofurfuryl alcohol.

Esters are especially chosen among liquid linear fatty esters—in particular isopropyl palmitate, myristyl stearate, octyl palmitate, isostearyl isostearate, butyl arachidonate, isopropyl lanolate, isopropyl myristate, glyceryl monostearate—, polyol esters—in particular, glycerol, ethylene, glycol, propylene glycol, diethylene glycol—, and oxyethylene esters.

Glycerides are especially monoglycerides, diglycerides, and triglycerides. Glycerides are especially chosen among vegetable oils, —in particular, olive oil, arachis oil, almond oil, hazelnut oil, sunflower oil, sesame oil, soya oil, maize oil, nut oil, grape seed oil, borage oil, evening primrose oil, rose tree muscatel oil, kiwi oil, avocado oil, cereal germ oil, *macadamia* oil, castor oil, poppy oil, cottonseed oil, apricot stone oil, coconut oil, copra oil, monoi oil, palm-kernel oil, carthame oil, crabwood oil, gourd seed oil, shark oil, mink oil—, butters,—in particular cocoa butter, shea butter, copra butter, babassu oil, palm oil, tamanu oil—, modified vegetable oils, synthetic oils, fats, and tallow.

According to the invention, the cerides used in the compositions are chosen especially among sterides, carotenecerides, lipochrome, waxes, in particular sperm whale or spermaceti, lanolin, lanolin derivatives, —lanolin wax, liquid lanolin, hydrogenated lanolin, ethoxylated lanolin, lanolin alcohols, acetylated lanolin alcohols, ethoxylated lanolin alcohols, lanolin acids, isopropyl lanolate—, jojoba oil, ozokerite, ceresin, carnauba wax, and bee wax.

According to the invention, surface active agents are especially emulsifying agents, wetting agents, detergents and/or foaming agents.

Cationic surface active agents are especially chosen among quaternary ammonium salts, fatty primary amine salts, quaternary ammonium starches, alkylpyridinium chlorides, alkyl ammonium saccharinates, diethylenetriamine starches or cationic resins.

Non-ionic surface active agents are especially chosen among glycerol esters, glycol esters, sorbitan esters, fatty alcohol ethers, lipophilic sucroesters, polyglycerol esters, propylene oxide ethylene oxide copolymers, saponins, ethoxylated fatty alcohols, glucose ethers, glycol ester or polyethylene glycol, glycol ester or polyglycerol, oxyethylenated sorbitan ester, oxyethylenated alkylphenols, aminoxides, self-emulsifiable bases (PEG esters), methyl glucoside derivatives, monoethanolamides, monoethanolamides derivatives, diethanolamides or diethanolamide derivatives.

Anionic surface active agents are especially chosen among alkaline soaps, amine soaps, alkylsarcosinates, alkylsulphoacetates, alkyltaurates, sodium or potassium alkyl sulphate, sodium or potassium ether alkyl sulphate, paraffins, olefin sulfonates, isethionates, sodium alkyl phosphates, sodium alkyl ether phosphates.

Amphoteric or zwitterionic surface active agents are especially chosen among alkylbetaines, alkylamidobetaines, alkylamino mono- or di-propionates, imidazole derivatives such as cocoamphodiacetate, and sodium lauroamphodiacetate.

According to the invention, the cosmetic and therapeutic composition can have, in addition to hydrolysed yeast proteins as defined above, other yeast components.

According to a preferred embodiment, the cosmetic or therapeutic composition, according to this invention, does not have any other yeast components, except for hydrolysed yeast proteins according to this invention.

This invention relates particularly to a cosmetic or therapeutic composition, as defined above, in which the said active substance has a moisturising effect, and/or a repairing effect, and/or a firmness effect, and/or an anti-aging effect, and/or an anti-seborrhoea effect, and/or an anti-acne effect, and/or an anti-dandruff effect, and/or a hair reconstruction effect, and/or an effect on hair brightness and/or smoothness and/or growth.

By the expression <<moisturising effect>>, it is designated a decrease in the skin evaporation due to an occlusive phenomenon or to a water fixation by an active substance, a humectant or hygroscopic effect of the active substance and/or a property of fixation for glycerides in the intercellular cement.

The moisturising effect of the composition, according to this invention, appears in particular, at the epidermis level, with an activation of the lipid synthesis, in particular phospholipids, neutral lipids, and the synthesis of hyaluronic acid.

The moisturising effect of the composition, according to this invention, can be emphasised in vitro by the study of the lipid synthesis and hyaluronic acid by the keratinocytes, as described in Example 3.

The moisturising effect of the composition, according to this invention, results also in an anti-dandruff effect at the time of an application of the said composition on the scalp.

The anti-dandruff effect can be emphasised by a decrease in the quantity of dandruff in a subject treated with the composition according to this invention, for example as described in Example 5.

By <<repairing effect>> or <<cicatrising effect>>, it is designated an effect on the epidermis and/or dermis repair and/or reconstruction. In particular, the repairing effect is useful for repairing injuries and/or burns.

In particular, the repairing effect of the hydrolysed yeast proteins is linked to the activation of the synthesis of hyaluronic acid. The repairing effect can be emphasised by a dosage of the liberation of hyaluronic acid and an analysis of its expression in reconstructed human epidermises, as described in Example 3.

By the expression <<firmness effect>>, it is designated a smooth and tonic effect of the skin results from its mechanical support, in particular collagen fibres and elastin.

According to the invention, the composition allows in particular to improve the contraction of collagen lattice, activate the elastin synthesis and the maturation of collagen.

Collagen lattice corresponds to a bundle of collagen fibres and fibrils.

According to the invention, the firmness effect of the composition can be emphasised in vitro, as described in example 3.

By the expression <<anti-aging effect>>, it is designated, at a time, a preventive effect to delay the appearance of the skin aging signs and an immediate effect to decrease aging signs. According to this invention, the composition has in particular an anti-aging effect linked to age and can also have an effect against photo-induced aging.

The visible signs of skin aging linked to age are, in particular, skin dryness, the appearance of little wrinkles, wrinkles, a decrease in skin thickness as well as a loss of skin suppleness.

Skin aging linked to age, results also in a decrease in the quantity of collagen, their solubility and synthesis, a decrease in the quantity of elastin and microfibrils, a decrease in the quantity of glycosaminoglycans and an inactivation of fibroblasts.

According to the invention, the anti-aging effect of the composition results, in particular, in an increase in the proliferation of dermis fibroblasts and their activity in terms of synthesis of collagen and glycosaminoglycans.

The anti-aging effect linked to age, can be emphasised in vitro by the increase in the synthesis of collagen and glycosaminoglycans by the dermis fibroblasts, as described in example 3.

In particular, the signs of photo-induced skin aging are the appearance of deep wrinkles, a thick and rough skin.

In particular, the photo-induced skin aging results in a decrease in the quantity and solubility of collagen, an increase in the quantity of elastin and microfibrils, an increase in glycosaminoglycans, an increase in inflammatory cells.

This invention relates also to a cosmetic or therapeutic composition, as defined above, characterised in that the active substance has a repairing effect.

By the expression <<anti-seborrhoea effect>>, it is designated an effect of regulation of sebaceous secretion, regulation of sebum adsorption and/or an astringent action allowing to close the skin pores.

According to the invention, the composition allows to reduce the sebum secretion.

In particular, according to the invention, the composition allows to regulate sebum adsorption through lipid adsorption.

Thus, according to the invention, the composition is particularly useful within the framework of a face hyperseborrhoea and/or a scalp hyperseborrhoea resulting in the so-called <<greasy>> hair.

According to the invention, the cosmetic composition has an anti-seborrhoea effect useful for greasy skins and/or acneic tendency.

By the expression <<anti-acne effect>>, it is designated a beneficial effect on acne.

In particular, according to the invention, the beneficial effect of the therapeutic composition on acne is linked to a regulation of sebaceous secretion.

The anti-seborrhoea and anti-acne effects can be emphasised, as described in example 4. For example, according to the invention, the composition is applied on the skin or scalp of subjects showing a hyperseborrhoea at the skin and scalp level, respectively. The sebum secretion is then assessed by applying a sebum absorbing patch on the part of the body treated. The patch is afterwards analysed to quantify the sebaceous secretion. The secretion after treatment is compared to the secretion in the same subject before treatment.

By <<reconstructing effect>>, it is designated the obtaining of a smooth effect of the hair. The outermost layer of a hair, called cuticle, is made up of scales overlapping each other. A reconstructing effect results in smooth relief of the cuticle, whereas damaged hair have a rough relief.

In particular, according to the invention, the composition has a toning effect on the hair.

The reconstructing effect of the hair can be emphasised by the measure of the hair topography, as described in example 5.

By <<brightness effect>>, it is designated the capacity of the hair to reflect the light and give the hair a shining effect.

By <<softness effect>>, it is designated the softness sensation of the hair upon touch.

By <<effect on hair growth>>, it is designated an increase in the growth kinetics of the hair.

The effect on hair growth can be emphasised by a measure test of the growth kinetics of the hair, as described in example 5.

This invention relates particularly to a cosmetic or therapeutic composition, as defined above, in the form of solution (one phase), dispersion (in particular an emulsion, suspension, foam or aerosol), gel, oil, stick, powder, wipe, mask or patch.

By <<emulsion>>, it is designated all types of emulsions and in particular, macroemulsions, microemulsions, nanoemulsions, simple emulsions, and multiple emulsions.

Emulsions are dispersions of a liquid into another liquid, the two liquids being non-mixable. Emulsions have a lipophilic, hydrophilic phase and an emulsifying agent.

In particular, emulsions include milks, lotions, creams, etc.

Nanoemulsions are dispersions in which the size of the particles dispersed has a diameter lower than 1,000 μm, in particular from 10 μm to 100 μm.

Nanoemulsions are dispersions in which the size of the particles dispersed has a diameter lower than 1,000 μm, in particular from 10 μm to 100 μm.

Nanoemulsions and microemulsions constitute transparent mediums.

In particular, according to the invention, the cosmetic or therapeutic composition is suited for skin or hair applications.

In particular, according to the invention, the composition for hair application is in the form of shampoos, lotions, masks, and sprays.

This invention relates to a cosmetic or therapeutic composition as defined above, in the form of tablet, wafer, dragée, capsule, granule, pill, powder, syrup, drinkable suspensions, and drinkable emulsion.

According to the invention, the cosmetic or therapeutic composition can have, as active substance, hydrolysed yeast proteins and at least one additional active substance.

By way of example, the additional active substance(s) can have a moisturising effect, and/or a firmness effect, and/or an anti-aging effect, and/or an anti-seborrhoea effect, and/or a hair reconstructing effect, and/or an effect on brightness, and/or softness, and/or hair growth, and/or repairing, and/or slimming, and/or cleaning, and/or anti-oxidant, and/or depigmenting, and/or vascular protector, and/or anti-inflammatory, and/or antibacterial, and/or antifungal.

According to the invention, in a preferred cosmetic composition, at least one additional active substance has the same cosmetic effect as the hydrolysed yeast proteins.

According to the invention, in a preferred therapeutic composition, at least one additional active substance has the same therapeutic effect as the hydrolysed yeast proteins.

Since hydrolysed yeast proteins and at least one additional active substance have the same cosmetic or therapeutic effect, the effect obtained is preferably a synergic effect.

Thus, according to the invention, the hydrolysed yeast proteins constitute a new natural agent, particularly useful for preparing cosmetic or therapeutic compositions.

This invention relates also to a preparation process of a cosmetic or therapeutic composition, consisting of the following stages:
protein hydrolysis of the yeast insoluble fraction in order to obtain hydrolysed yeast proteins, and
blending of the said hydrolysed yeast proteins with an acceptable cosmetic or therapeutic vehicle.

In particular, the acceptable cosmetic or therapeutic vehicle is chosen among the above mentioned additives and/or excipients.

This invention relates also to a preparation process, as defined above, of a cosmetic or therapeutic composition, consisting of the following stages:
protein hydrolysis of the yeast insoluble fraction in order to obtain hydrolysed yeast proteins, and
blending of the said hydrolysed yeast proteins with at least an additional active substance and an acceptable cosmetic or therapeutic vehicle.

This invention relates also to the use of hydrolysed yeast proteins obtained from the yeast insoluble fraction as active substance in cosmetic and/or therapeutic compositions.

This invention relates particularly to the use as defined above, characterised in that the said hydrolysed yeast proteins are obtained from the yeast insoluble fraction.

This invention relates particularly to the use as defined above, characterised in that the said hydrolysed yeast proteins are obtained through enzymatic hydrolysis and/or acid hydrolysis and/or alkaline hydrolysis.

This invention relates to the use as defined above, characterised in that the said hydrolysed yeast proteins are obtained through enzymatic hydrolysis with at least a peptidase, preferably chosen among papain, trypsin, chymotrypsin, subtilisin, pepsin, thermolysin, pronase, flavastacine, enterokinase, factor Xa protease, furin, bromelain, proteinase K, genenase I, thermitase, carboxypeptidase A, carboxypeptidase B, collagenase, Alcalase®, Neutrase® and/or their blending.

In particular, this invention relates to the use as defined above, characterised in that the said yeast hydrolysed proteins are obtained from yeasts of Saccharomyces, Kluyveromyces, Torula, Candida, Hansenula, Pichia genus, and/or their blending, preferably Saccharomyces, advantageously Saccharomyces cerevisiae.

This invention relates also to the use as defined above, characterised in that the said yeast hydrolysed proteins have at least 40%, preferably at least 45%, more preferably at least 50%, even more preferably at least 55%, even more preferably at least 60% of yeast proteins with a molecular weight ranging between 1 and 5 kDa.

This invention relates also to the use as defined above, characterised in that the said yeast hydrolysed proteins have at most 55%, preferably at most 50%, more preferably at most 45%, even more preferably at most 40%, even more preferably at most 35% of hydrolysed yeast proteins with a molecular weight lower than 1 kDa.

This invention relates also to the use as defined above, characterised in that the AN/TN ratio of the said hydrolysed yeast proteins is lower or equal to 35%, in particular lower or equal to 30%, in particular lower or equal to 25%, in particular lower or equal to 20%.

This invention relates particularly to the use as defined above, characterised in that the said hydrolysed yeast proteins are present in the cosmetic or therapeutic composition at the rate of 0.001% to 20%, more preferably from 0.001% to 15% of hydrolysed yeast proteins, even more preferably from 0.001% to 10% of hydrolysed yeast proteins, even more preferably from 0.01% to 3% of hydrolysed yeast proteins, even more preferably from 0.01% to 2% of hydrolysed yeast proteins.

This invention relates to the use as defined above, characterised in that the said cosmetic or therapeutic composition have at least one additive chosen among preservatives, chelating agents, colouring agents, UV filter, pH regulator, texturising agents, perfume or antioxidant, and at least one excipient chosen among hydrophilic compounds, hydrophobic compounds or surface active agents.

This invention relates to a method for cosmetic treatment comprising a stage of contact with the skin and/or skin appendages and/or mucous membranes of a cosmetic composition as defined above or liable to be obtained through the preparation process as defined above.

The term <<contact>>, later will also be called <<application>>.

The treatment method can include one or more applications a day, preferably from one to three applications a day.

The frequency of applications of the cosmetic composition can be reduced during treatment.

The method for cosmetic treatment can consist in a short treatment, from one to more weeks, or a long-term treatment on many years. The method for treatment can also consist in a treatment in the form of renewed cures every year or several times in a year.

This invention relates particularly to a method for cosmetic treatment as defined above, designated to moisturise skin and/or mucous membranes and/or skin appendages, and/or improve the repair of skin and/or mucous membranes and/or skin appendages, and/or improve dermis firmness, and/or fight against skin aging, and/or regulate sebum secretion, and/or reduce dandruff, and/or repair hair, and/or improve hair growth.

The epidermis moisturising aims, at a time, at restoring the quality of the skin barrier, namely an impermeability limiting water evaporation, and favouring the presence of molecules trapping water, namely glycosaminoglycans, in particular hyaluronic acid.

According to the invention, the method for cosmetic treatment is particularly useful in the treatment and/or prevention of skin dryness and dandruff.

The repair of the skin and/or mucous membranes and/or skin appendages aims at helping the physiological healing, in particular by activating the synthesis of hyaluronic acid.

Skin tightening aims at maintaining or reinforcing skin firmness, in particular by activating the synthesis of elastin, the synthesis and maturation of collagen and the contraction of collagen lattice.

The fight against skin aging relates to the delay and/or reduction of aging signs.

According to an advantageous embodiment of the invention, the treatment designated to fight against skin aging is associated to an epidermis moisturising.

According to the invention, the method for cosmetic treatment is particularly advocated for subjects from 20 years, in particular from 30 years, in particular from 40 years, in particular from 50 years.

In particular, the regulation of sebum secretion relates to the reduction of sebum secretion.

According to the invention, the method for cosmetic treatment is particularly useful for regulating the seborrhoea of greasy skins, in particular for greasy skins said <<with problems>> or <<with acneic tendency>> and/or for hair so-called <<greasy>>.

The hair repair consists in the reconstruction of the hair, in particular by smoothing hair cuticle and/or restoring brightness and/or softness to hair.

According to the invention, the method for cosmetic treatment is particularly appropriate for subject with damaged hair, in particular following to a sun exposure, sea, too frequent washings, colourings, brushings, perms, etc.

The improvement of the hair growth aims at increasing hair growth kinetics, also called hair growth.

According to the invention, the method for cosmetic treatment is particularly appropriate for subject with slow hair growth kinetics and/or in case of normal hair loss.

In particular, a hair loss said normal, corresponds to androgenogenetic alopecia, endocrine alopecia, or alopecia linked to age.

According to an advantageous embodiment, the method for cosmetic treatment, according to the invention, is appropriate for a face application, in particular on the eye contour, nose, forehead, chin, body, in particular on the hands, feet, back, hair and/or scalp.

This invention relates also to hydrolyse yeast proteins obtained from the yeast insoluble fraction for their use as medicine, preferably for the treatment and/or prevention of pathological dry skin, pathological healing problems and/or pathological hyperseborrhoea, and/or acne.

In particular, this invention relates to hydrolysed yeast proteins as defined above or liable to be obtained through the preparation process as defined above, for the treatment and/or prevention of pathological dry skin, pathological healing problems and/or pathological hyperseborrhoea, and/or acne, and/or pathological hair loss. This invention aims at using them for preparing a therapeutic composition as defined above.

According to the invention, the therapeutic composition is particularly useful for the treatment of pathological skin dryness, also called xerosis, in particular in case of ichthyosis, skin dryness associated to eczema or psoriasis or pathological scalp dryness, in particular associated to dandruff.

According to the invention, the therapeutic composition is particularly useful for the treatment of pathological healing, such as hypertrophic healing, keloid healing, and retractile cicatrisation and/or healing delays, in particular delays linked to a poor asepsis, a vascular and/or neurological origin.

According to the invention, the therapeutic composition is also useful for the treatment of pathological hyperseborrhoea, in particular associated to a hormonal deregulation, in particular in teenager, pregnant woman, or menopause woman.

According to this invention, the therapeutic composition is also useful for the treatment of pathological acne, in particular juvenile acne associated to hyperseborrhoea.

According to the invention, the therapeutic composition is also useful for the treatment of pathological hair loss, also called pelade, resulting from an emotional shock, thyroid disorder, and/or treatments having alopecia as side effect (for example anti-cancer treatments)

In particular, the use as defined above is intended to a local application of the said therapeutic composition on the skin and/or skin appendages and/or mucous membranes.

The use as defined above can consist in one or more applications a day, preferably from one to three applications a day.

The frequency of applications of the therapeutic composition can be reduced during treatment.

The therapeutic treatment can consist in an acute treatment, from a few days to several weeks, or a chronic treatment on several years. The treatment can also consist in a treatment in the form of renewed cures every year or several times in a year.

This invention relates also to the use of a cosmetic composition or a therapeutic composition as defined above, intended to the treatment of the side effects or unpleasant manifestations of other treatments.

In particular, said side effects or unpleasant manifestations result in skin dryness, for example associated to eczema.

EXAMPLES

The invention is illustrated below with the following non limiting examples:

Example 1

Obtaining of Hydrolysed Yeast Proteins According to this Invention Equipment and Methods An aqueous suspension of yeast cells of *Saccharomyces cerevisiae*, having a content of dry matter within 12 and 30% by mass, is subjected to a thermal treatment from 1 to 3 hours within 70° C. and 90° C. (in order to deactivate the endogenous cell enzymes). This thermal treatment induces a yeast plasmolysis that allows separating thereafter the insoluble fraction from the soluble fraction, being the soluble fraction limited. The separation of the solubilised fraction from the insoluble fraction is carried out through several successive stages of centrifugation and washing with water (at least 2 successive stages, preferably at least 3).

The insoluble fraction recovered, having a content of dry matter within 12 and 25% by mass, is then hydrolysed by adding at least one exogenous protease during at least 18 hours at a temperature of 45° C. to 65° C. For example, the protease is the papain used at a concentration of 0.01% to 0.5% (weight/weight).

The solubilised hydrolysed fraction is separated from the hydrolysed insoluble fraction through several successive stages of centrifugation and washing with water (at least 2 successive stages, preferably at least 3).

The solubilised hydrolysed fraction is concentrated through at least one vacuum continuous or batch evaporation stage, in order to obtain a concentrated fraction. The concentrated fraction is possibly purified through filtration or clarification before being dried through atomisation.

The solubilised hydrolysed and possibly concentrated and/or purified and/or dried fraction so obtained, corresponds to the hydrolysed yeast proteins according to this invention.

The molecular weight and the molecular weight profile of the hydrolysed yeast proteins are determined through liquid gel permeation chromatography with UV detection at 215 nm on a SEPHADEX Pharmacia HR 10/30 gel filtration column. The calibration is carried out through protein standards with known size that allows calibrating the system and assessing the molecular weight of a blending.

The AN/TN ratio is calculated by measuring total nitrogen and amino nitrogen.

Total nitrogen (TN) is determined through the Kjeldahl method, a method established starting from the <<official methods of analysis for dietetic products>> (JO of 3 Nov. 1979).

The amino nitrogen (AN) is determined through NQS derivatisation (1-2 naphtoquinone 4-sulfonatc (H. NEHRING, A. HOCK, improved method for determination aminonitroaen, Pharmazie, 1971, 26, 616-619).

Results

According to this invention, the hydrolysed yeast proteins obtained from the concentrated solubilised hydrolysed fraction, purified and dried, are afterwards marked by letter <<A>>. They have a light beige colour.

Figure 1:
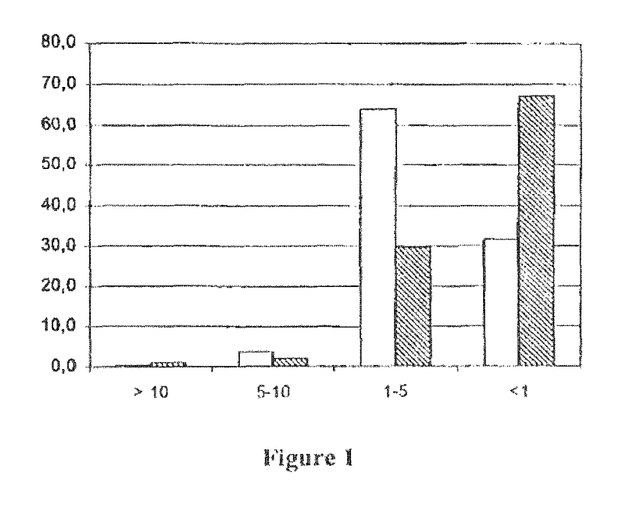
FIG. 1 represents, in percentage, the size distribution (in kDa) within the hydrolysed yeast proteins according to the invention (white histogram) and within hydrolysed yeast proteins obtained from the hydrolysis of yeast whole cells (striped histogram).

Table 1 and FIG. 1 indicate the distribution of the molecular weights within hydrolysed yeast proteins according to this invention (A), compared to that of hydrolysed yeast proteins (B) obtained from hydrolysis of the yeast whole cell.

B hydrolysed yeast proteins are obtained through thermal treatment of a suspension of *Saccharomyces cerevisiae* yeast cells from 1 to 3 h within 70° C. and 90° C., then with the addition of at least one exogenous protease during at least 18 hours at a temperature of 45° C. to 65° C. For example, the protease is the papain used at a concentration of 0.01% to 0.5% (weight/weight). The solubilised hydrolysed fraction is separated from the hydrolysed insoluble fraction through several successive stages of centrifugation and washing with water (at least 2 successive stages, preferably at least 3). The solubilised hydrolysed fraction is concentrated through at least one vacuum continuous or batch evaporation stage, in order to obtain a concentrated fraction. The concentrated fraction is possibly purified through filtration or clarification before being dried through atomisation in order to obtain hydrolysed yeast proteins of whole yeasts (B).

According to the invention, most of the hydrolysed proteins have in the hydrolysed yeast proteins (A), a molecular weight higher or equal to 1 kDa and lower than 5 kDa (64.2%); the other hydrolysed proteins have essentially a molecular weight lower than 1 kDa (31.6%).

Being a matter of yeast proteins obtained from whole cells (B), the distribution of molecular weights is completely different: most of the hydrolysed proteins have a molecular weight lower than 1 kDa (67.3%), the other hydrolysed proteins having essentially a molecular weight higher or equal to 1 kDa.

TABLE 1

| Molecular weight | Distribution (in percentage) | |
|---|---|---|
| (in kDa) | A | B |
| ≥10 | 0.3 | 1.1 |
| ≥5 and <10 | 3.9 | 2.0 |
| ≥1 to <5 | 64.2 | 29.6 |
| <1 | 31.6 | 67.3 |

Figure 2:
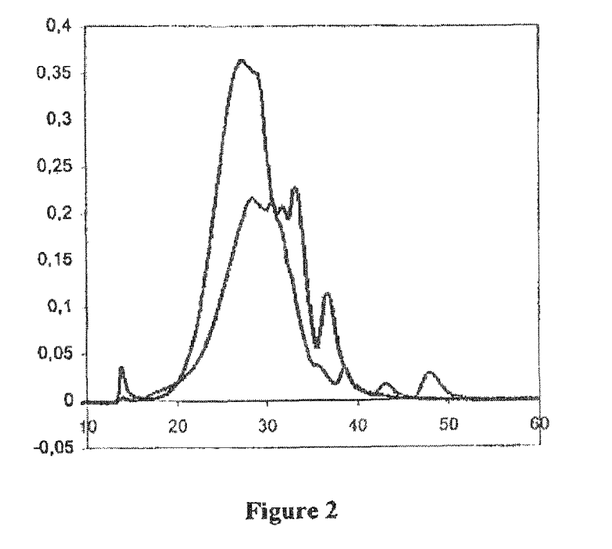
FIG. 2 represents the molecular weight profile of hydrolysed yeast proteins according to the invention (black curve) and that of hydrolysed yeast proteins obtained from the hydrolysis of yeast whole cells (grey curve). The coordinate axis indicates the absorption read at 214 nm and the abscissa axis the retention time in minutes.

According to the invention, the difference between the molecular weight profile of hydrolysed yeast proteins and that of yeast proteins obtained from the hydrolysis of whole cells is also clearly visible in FIG. 2.

In FIG. 2, the products that are represented first, have the higher molecular weight. The hydrolysed yeast proteins appear more concentrated on a range of high molecular weights with a more important intensity. The hydrolysed proteins of B composition show a peak concentration towards weaker molecular weights, which is representative of a greater degradation.

With reference to AN/TN ratio, table 2 indicates that hydrolysed yeast proteins according to this invention (A), have an AN/TN ratio ranging between 15 and 28%, whereas that of the hydrolysed yeast proteins obtained from whole cells (B), ranges between 32 and 40%.

TABLE 2

| | A | B |
|---|---|---|
| AN/TN (in percentage) | 15-28 | 32-40 |

The AN/TN ratio gives an estimation of protein degradation: the weaker it is, the more the proteins are in the native form and inversely, the higher it is, the more the proteins are in the degraded form.

Table 3 shows that hydrolysed yeast proteins according to the invention (A), in effect, have very few free amino acids, compared to hydrolysed yeast proteins obtained from whole cells (B).

Hence, the hydrolysed yeast proteins according to this invention (A), show a lower degradation rate than the hydrolysed yeast proteins of B composition.

Furthermore, table 3 also shows that the composition in amino acids of hydrolysed yeast proteins according to this invention (A), is different from that of hydrolysed yeast proteins obtained from whole cells (B).

TABLE 3

|  | A (% g/g) | | B (% g/g) | |
| --- | --- | --- | --- | --- |
|  | free amino acids | total amino acids | free amino acids | total amino acids |
| ASP | Nd | 7.59 | 0.7 | 6 |
| SER | Nd | 3.62 | 1.4 | 2.8 |
| GLU | 0.47 | 10.51 | 5.5 | 13.2 |
| GLY | Nd | 3 | 0.6 | 3 |
| HIS | Nd | 1.61 | 0.5 | 1.3 |
| ARG | Nd | 2.38 | 1.2 | 3.4 |
| THR | Nd | 4.26 | 1.1 | 3.2 |
| ALA | Nd | 4.75 | 2.9 | 5.1 |
| PRO | Nd | 2.93 | 0.5 | 3.8 |
| CYS | Nd | 0.2 | 0.1 | 0.3 |
| TYR | Nd | 1.89 | 0.3 | 1.5 |
| VAL | Nd | 4 | 1.3 | 3.6 |
| MET | Nd | 0.56 | 0.4 | 0.8 |
| LYS | Nd | 6.23 | 1.5 | 5 |
| ILE | Nd | 3.42 | 1 | 3 |
| LEU | Nd | 5.52 | 2.1 | 4.6 |
| PHE | Nd | 2.94 | 1.1 | 2.5 |
| Total | 0.47 | 65.41 | 22 | 63.1 |

(Nd: Not determined (values are too weak)

Example 2

Effect of the Hydrolysed Yeast Proteins According to the Invention on the Expression Profile of Keratinocytes and Fibroblasts Equipment and Methods The effect of the hydrolysed yeast proteins according to the invention on the expression profile of normal human epidermal keratinocytes and normal human dermal fibroblasts is valued on DNA microarrays.

The first microarray has 164 genes of human keratinocytes, especially involved in cell growth, differentiation, adhesion, communication, and death.

The second microarray has 143 genes of human fibroblasts, especially involved in cell growth, adhesion, communication, synthesis and extracellular matrix degradation and stress.

Normal human epidermal keratinocytes and normal human dermal fibroblasts are cultured for 24 h or 96 h in the presence or absence of hydrolysed yeast proteins of example 1. Cells are then washed and their RNA is extracted and purified, cDNA is obtained from this RNA through reverse transcription. The cDNAs obtained are then marked before being hybridised on the microarray corresponding to the same cell type.

The expression level of each gene in the absence of hydrolysed yeast proteins is compared to the expression level obtained in the presence of the said hydrolysed yeast proteins.

Results

Among the genes activated on the microarray of dermal fibroblasts, there are genes involved in the cell proliferation and synthesis of the extracellular matrix.

The results obtained on the microarray of epidermal keratinocytes show that the hydrolysed yeast proteins, according to this invention, stimulate the differentiation of epidermal keratinocytes and inhibit the expression of genes coding for proteins of cellular matrix, which implies a moisturising effect. The phenomenon of keratinocyte differentiation is indeed implied in the reinforcement of the skin barrier and allows to limit water losses. The inhibition of gene expression coding for proteins of cellular matrix goes in the same direction.

Example 3

Moisturising, Anti-Aging and Firmness Properties of Hydrolysed Yeast Proteins According to the Invention Equipment and Methods The hydrolysed yeast proteins used, are those described in example 1.

(i) Moisturising Effect

Tests are carried out on normal human epidermal keratinocytes NHEK seeded in the wells of a 96-well plate in a KSFM medium (without scrum). The lipid synthesis, the FLG (filaggrin), CK10 (cytokeratin) and TGK (transglutaminase K) synthesis and the hyaluronic acid synthesis, are assessed in the presence of different concentrations of hydrolysed yeast proteins (from 0.04 mg/ml to 1 mg/ml). Three culture wells are made under condition.

Calcium is used as positive control for lipid synthesis and FLG, CK10, TGK synthesis and retinoic acid as positive control for hyaluronic acid synthesis.

Negative control is constituted by the sole culture medium.

Lipid synthesis is analysed through Phosphoimaging and the hyaluronic acid synthesis is assessed through a measurement of the hyaluronic acid concentration freed in the medium.

FLG, CK10 synthesis is assessed through cell immunomarking after 72 hours of culture, and the TGK synthesis through cell immunomarking after 48 hours.

(ii) Anti-Aging Effect

Normal human dermal fibroblasts (NHDF) and normal human dermal aged fibroblasts (AgNHDF) are seeded in the wells of a 96-well plate in a DMEM medium+10% SVF. Tests are carried out in DMEM medium+1% SVP.

The test for fibroblast proliferation and the test for glycosaminoglycan and collagen synthesis are carried out in the presence of different concentrations of hydrolysed yeast proteins. Three culture wells are made under condition.

Negative control is constituted by the sole culture medium.

The proliferation test is carried out 24 h after cell-seeding. [$^3$H]-thymidine is added in the culture milieu. The EGF is used as positive control.

Glycosaminoglycan and collagen synthesis is assessed on 80% confluence cells, to which [$^3$H]-glucosamine or [$^3$H]-proline is added, respectively. The retinoic acid is then used as positive control.

After 24 hours of incubation, the macromolecules are extracted and the incorporation of radioactive precursors is measured.

(iii) Firmness Effect

Tests are carried out on normal human dermal aged fibroblasts (AgNHDF).

The synthesis and maturation of collagen are assessed after pre-culture of flask cells for 8 days in the presence of different concentrations of hydrolysed yeast proteins. The negative control is constituted by the sole culture medium and the positive control by TGFβ and C vitamin. The cells are then seeded in culture chamber. Just before confluence, cells are fixed in methanol and the presence of collagen is detected through immunohistochemistry by using a specific antibody directed against collagen I and a secondary fluorescent antibody. The expression level of the intracellular and extracellular collagen and their localisation around the matrix are analysed through the microscope.

The contraction of collagen lattice is assessed after culture of flask cells for 8 days in the presence of different concentrations of hydrolysed yeast proteins. The negative control is constituted by the sole culture medium and the positive control by TGFβ. The cellular suspension obtained is then introduced in a collagen I solution under controlled pH. After a few hours, the solution jellifies in such a manner as to obtain an equivalent dermis, the contour of which, is clearly defined. The diameter and number of the cells of each equivalent dermis are measured by following a defined kinetics.

The elastin synthesis is assessed after culture of flask cells for 8 days in the presence of different concentrations of hydrolysed yeast proteins. The negative control is constituted by the sole culture medium and the positive control by C vitamin. The cells are then seeded in culture chamber. Just before confluence, cells are fixed in methanol and the presence of elastin is detected through immunohistochemistry by using a specific antibody directed against elastin and a secondary fluorescent antibody. The expression level of elastin is analysed through the microscope.

(iv) Repairing Effect

Tests are carried out on reconstructed human epidermises. The reconstructed epidermises are cultured. On the $5^{th}$ day, cultures are treated with hydrolysed yeast proteins tested at 3 concentrations in local application.

Negative control is constituted by a non-treated culture, the positive control by retinoic acid in local application. The treatments are renewed on the $7^{th}$ day and cultures are stopped on the $10^{th}$ day.

Freeing of hyaluronic acid in the medium is dosed on the culture supernatants by means of a specific modified Elisa test. The results are expressed in µg/ml of liberated hyaluronic acid and in stimulation percentage with respect to untreated control.

The expression of hyaluronic acid in the epidermises is assessed through immunohistology.

(v) Statistics

Intergroup comparisons are carried out through the analysis of variance (ANOVA) with the aid of a Dunnett multiple comparison test.

Results (i) Assessment of the Moisturising Effect on Epidermis

In the presence of the hydrolysed yeast protein solution, the lipid and hyaluronic acid synthesis by keratinocytes is activated with respect to negative control.

In addition, in the presence of the hydrolysed yeast protein solution, a stimulation of FLG, CK10 and TGK secretion is observed, with a dose-effect.

(ii) Assessment of the Anti-Aging Effect on Dermis

In the presence of the hydrolysed yeast protein solution, an activation of the cell proliferation and an increase in the synthesis of the major components of the extracellular matrix is observed (with respect to negative control).

(iii) Assessment of the Firmness Effect

In the presence of the hydrolysed yeast protein solution, an increase in the collagen expression level is observed, as well as a maturation of the collagen revealed by its deposition around the matrix, with respect to negative control. The density increase in the dermis equivalent (by diameter ratio on number of weaker cells than that of the negative control) conveys a better contraction of the collagen lattice. In addition, the elastin synthesis by fibroblasts is activated with respect to negative control. All these elements indicate that hydrolysed yeast proteins improve the biomechanical qualities of dermis (in particular, in terms of elasticity and compressibility).

(iv) Assessment of the Repairing Effect

In the presence of the hydrolysed yeast protein solution, an increase in the hyaluronic acid expression is observed (with respect to negative control).

Example 4

Anti-Seborrhoea and Anti-Acne Properties

Equipment and Methods

The hydrolysed yeast protein solution is applied on the skin or scalp of subjects showing a hyperseborrhoea at the skin or scalp level, respectively.

The sebum secretion is then assessed by applying a sebum absorbing patch on the part of the body treated. The patch is afterwards analysed to quantify the sebaceous secretion.

The secretion alter treatment is compared to the secretion in the same subject before treatment.

Results

The hydrolysed yeast protein solution allows reducing the quantity of sebum secreted.

Example 5

Hair Applications

Equipment and Methods (i) Hydrolysed Yeast Proteins

The hydrolysed yeast protein solution is that described in the example 1.

(ii) Anti-Dandruff Effect

The hydrolysed yeast protein solution is applied on the scalp of subjects suffering from dandruff. After treatment with the hydrolysed yeast protein solution, a patch is applied on the treated zone to recover the scalp dandruff.

The quantity of dandruff recovered on the patch is compared before and after treatment.

(iii) Hair Growth

The hair growth kinetics is assessed in the following way: before treatment, a lock of hair of a subject is coloured from the root for 2 to 3 cm; the hydrolysed yeast protein solution is then applied on the scalp; the distance between the root and the beginning of colouring is measured.

The growth kinetics after treatment of a group of treated subjects is compared to that obtained with a group of untreated subjects.

(iv) Hair Brightness

Hair brightness is determined by measuring the quantity and intensity of light reflected on the hair surface. To this purpose, photos of hair are taken with crossed polarisation and non-polarisation. The two photos are then converted into levels of grey and hair brightness is obtained through subtraction of the light between the two photos.

Hair brightness after applying the hydrolysed yeast protein solution is compared to that obtained before treatment.

(v) Hair Softness

Hair softness is assessed through a sensory analysis by a board of examiners made up of three qualified persons to assess hair softness upon touch.

Hair softness is noted on a 0 to 10 scale, where note 0 corresponds to an absence of softness and note 10 to a great softness.

Hair softness after applying the hydrolysed yeast protein solution is compared to that obtained before treatment.

(vi) Hair Reconstruction

Hair reconstruction is assessed by measuring the hair surface topography with an interferometric microscope.

The parameters allowing determining the condition of the cuticle scales along the hair are the following:
- opening of scales
- length of scales
- surface topology, namely roughness The analysed surface measures 120×30 μm.

Hair reconstruction after applying the hydrolysed yeast protein solution is compared to the hair status before treatment.

Results

Hair application of the hydrolysed yeast protein solution allows the obtaining of an anti-dandruff effect and an increase of the hair growth.

Hydrolysed yeast protein solution has also a hair repairing effect, by allowing the improvement of brightness, softness, and hair reconstruction. In particular, a reduction in the number of cuticle scale openings, an increase in the length of scales and a decrease in roughness, is observed.

Example 6

Examples of Cosmetic Compositions and Therapeutic Compositions According to this Invention The following compositions constitute non-exhaustive examples of this invention.

Composition 1

Moisturising Cream (Oil in Water)

| Ingredients | Percentage (weight/weight) |
| --- | --- |
| Hydrolysed yeast proteins (A composition) | 1.5 |
| Caprylic and capryc triglyceride | 4 |
| Mineral oil | 2 |
| Stearyl alcohol | 3 |
| Isopropyl palmitate | 2 |
| Glycerol stearate PEG-100 | 6 |
| Dimethicone | 4 |
| Glycerine | 8 |
| Preservative | 0.3 |
| Water | 69.2 |

Composition 2

Lotion (Oil in Water)

| Ingredients | Percentage (weight/weight) |
| --- | --- |
| Hydrolysed yeast proteins (A composition) | 2.50 |
| paraffin oil | 2.60 |
| Propylene glycol | 1.40 |
| triglyceride | 1.0 |
| PEG-75 | 1.0 |
| Coco-caprylate caprate | 1.0 |
| Glycerol stearate | 0.6 |
| Dimethicone | 0.5 |
| Polyacrylic acid | 0.3 |
| Sodium hydroxide | 0.11 |
| perfume | 0.10 |
| EDTA | 0.03 |
| glycerine | 5.00 |
| colour | 0.32 |
| preservative | 1.50 |
| purified water | 82.04 |

Composition 3

Anti-Dandruff Shampoo

| Ingredients | Percentage (weight/weight) |
| --- | --- |
| Hydrolysed yeast proteins (A composition) | 1.5 |
| Sodium lauryl sulfate | 30 |
| Disodium Laureth sulfate | |
| Cocoamphodiacetate | |
| Hexylene glycol | |
| Cocamidopropylamine oxide | 1 |
| Extract of Indian watercress | 1 |
| Preservative | 0.2 |
| Citric acid | pH 6 |
| water | spp 100 |

Composition 4

Moisturising Mask

| Ingredients | Percentage (weight/weight) |
| --- | --- |
| Hydrolysed yeast proteins (A composition) | 4.00 |
| Timiron flash | 4.00 |
| Propylene glycol | 3.00 |
| glycerine | 3.00 |
| urea | 3.00 |
| Mucic acid | 0.30 |
| perfume | 0.30 |
| Arabic gum | 0.50 |
| Xanthan gum | 0.10 |
| EDTA | 0.10 |
| allantoin | 0.10 |
| Sodium hydroxide | 0.06 |
| Polyvinyl alcohol | 10.00 |
| talc | 10.00 |
| 95% Alcohol | 15.00 |
| Purified water | 46.54 |

What is claimed is:

1. A method for treating a skin or skin appendage condition in a subject, the method comprising a step of administering to the subject a composition comprising hydrolysed yeast proteins,
wherein the hydrolysed yeast proteins comprise at least 40% of yeast proteins with a molecular weight ranging from 1 to 5 kDa and are obtained by:
submitting *Saccharomyces cerevisiae* yeast cells to a thermal treatment carried out for 1 to 3 hours at between 70° C. and 90° C.,
separating yeast hulls after thermal treatment of yeast, and submitting the yeast hulls to exogenous enzymatic hydrolysis with at least one peptidase for at least 18 hours at a temperature of between 45° C. and 65° C. to produce a reaction mixture comprising hydrolyzed yeast proteins, and separating the hydrolyzed yeast proteins from the reaction mixture, wherein treating a skin or skin appendage condition is selected from the group consisting of: treating dry skin, reducing sebum secretion, treating skin aging, promoting skin firmness, treating dandruff, promoting hair brightness and softness, and any combination thereof.

2. The method according to claim 1, wherein administering the composition to the subject comprises contacting the skin or skin appendage of the subject with the composition.

3. The method according to claim 1, wherein dry skin is associated to ichthyosis, eczema or psoriasis.

4. The method according to claim 1, wherein the yeast hulls are separated by centrifugation.

5. The method according to claim 1, wherein the at least one peptidase is selected from the group consisting of papain, trypsin, chymotrypsin, subtilisin, pepsin, thermolysin, pronase, flavastacine, enterokinase, factor Xa protease, furin, bromelain, proteinase K, generase I, thermitase, carboxypeptidase A, carboxypeptidase B, collagenase, and mixtures thereof.

6. The method according to claim 5, wherein the at least one peptidase is papain.

7. The method according to claim 6, wherein the papain is used at a concentration of 0.01% to 0.3% w/w.

8. The method according to claim 1, wherein the hydrolysed yeast proteins comprise at least 60% of yeast proteins with a molecular weight ranging from 1 to 5 kDa.

9. The method according to claim 1, wherein the hydrolysed yeast proteins comprise at most 55% of yeast proteins with a molecular weight lower than 1 kDa.

10. The method according to claim 1, wherein the hydrolysed yeast proteins comprise at most 35% of hydrolysed yeast proteins with a molecular weight lower than 1 kDa.

11. The method according to claim 1, wherein the composition comprises from 0.001% to 20% of hydrolysed yeast proteins.

12. The method according to claim 11, wherein the composition comprises from 0.01% to 2% of hydrolysed yeast proteins.

13. The method according to claim 1, wherein the hydrolysed yeast proteins have an AN/TN ratio lower than or equal to 35%.

14. The method according to claim 1, wherein the hydrolysed yeast proteins have an AN/TN ratio lower than or equal to 20%.

15. The method according to claim 1, wherein the composition further comprises at least one additive selected from the group consisting of preservatives, chelating agents, colouring agents, UV filters, pH regulators, texturizing agents, perfumes, and antioxidants.

16. The method according to claim 1, wherein the composition further comprises at least one excipient selected from the group consisting of hydrophilic excipients, hydrophobic excipients and surfactants.

17. The method according to claim 1, wherein the *Saccharomyces cerevisiae* yeast cells have a dry matter content of between 12% and 30% by mass.

18. The method according to claim 1, wherein the yeast hulls have a dry matter content of between 12% and 25 by mass.

* * * * *